(12) United States Patent
Manus

(10) Patent No.: US 10,456,214 B2
(45) Date of Patent: Oct. 29, 2019

(54) LIGHT POINT IDENTIFICATION METHOD

(71) Applicant: Brainlab AG, Munich (DE)

(72) Inventor: Johannes Manus, Munich (DE)

(73) Assignee: Brainlab AG, Munich (DE)

( * ) Notice: Subject to any disclaimer, the term of this patent is extended or adjusted under 35 U.S.C. 154(b) by 226 days.

(21) Appl. No.: 15/543,053

(22) PCT Filed: Jan. 28, 2015

(86) PCT No.: PCT/EP2015/051712
§ 371 (c)(1),
(2) Date: Jul. 12, 2017

(87) PCT Pub. No.: WO2016/119840
PCT Pub. Date: Aug. 4, 2016

(65) Prior Publication Data
US 2018/0008371 A1  Jan. 11, 2018

(51) Int. Cl.
*G06K 9/00* (2006.01)
*A61B 90/00* (2016.01)
*A61B 34/20* (2016.01)
*A61B 90/30* (2016.01)
*G06T 7/521* (2017.01)

(52) U.S. Cl.
CPC .............. *A61B 90/39* (2016.02); *A61B 34/20* (2016.02); *A61B 90/30* (2016.02); *A61B 90/36* (2016.02); *A61B 90/361* (2016.02); *G06T 7/521* (2017.01); *A61B 2034/2055* (2016.02); *A61B 2034/2057* (2016.02); *A61B 2034/2065* (2016.02); *A61B 2090/364* (2016.02); *A61B 2090/371* (2016.02); *A61B 2090/3937* (2016.02)

(58) Field of Classification Search
CPC .... A61B 2560/0295; A61B 2560/0412; A61B 5/0002; A61B 5/0006; A61B 5/02438
USPC ........... 382/128; 600/407, 424, 431; 378/65; 606/4; 348/77
See application file for complete search history.

(56) References Cited

U.S. PATENT DOCUMENTS 6,346,933 B1   2/2002  Lin
2002/0002330 A1  1/2002  Vilsmeier
(Continued)

FOREIGN PATENT DOCUMENTS

| CN | 101419513 | 4/2009 |
| WO | 2011047467 A1 | 4/2011 |
| WO | 2013134782 A1 | 9/2013 |

OTHER PUBLICATIONS

European Patent Office, International Search Report and Written Opinion from corresponding International Application No. PCT/EP2015/051712, dated May 1, 2016, pp. 1-12.

*Primary Examiner* — Charlotte M Baker
(74) *Attorney, Agent, or Firm* — Tucker Ellis LLP

(57) ABSTRACT

A data processing method performed by a computer for detecting reflections of light pulses, comprising the steps: acquiring a camera signal representing a series of camera images of a camera viewing field; detecting whether the camera signal includes one or more light mark portions within the camera viewing field possibly representing a light pulse reflection; relating the detected light mark portions in the series of camera images to a pre-defined emission pattern of the light pulses; and determining that a light mark portion is a reflected light pulse, if the light mark portion in the series of camera images matches to the pre-defined emission pattern of the light pulses.

10 Claims, 3 Drawing Sheets

(56) References Cited

U.S. PATENT DOCUMENTS

2008/0009954 A1    1/2008   Mueller et al.
2012/0229622 A1    9/2012   Goldberg et al.

LIGHT POINT IDENTIFICATION METHOD

RELATED APPLICATION DATA

This application is a national phase application of International Application No. PCT/EP2015/051712, filed Jan. 28, 2015 and published in the English language.

FIELD OF THE INVENTION

The present invention relates in general to a (laser) pointer system and a data processing method for detecting or identifying reflections of light pulses which can be used for determining a shape of a surface or registering a surface to a pre-defined shape. The detection of reflections serves the purpose of identifying light points which originate from an optical pointer used or held for example by a person and which do not originate from other sources. A patient or a patient body part can for example be registered in a camera-assisted medical navigation system using the 3D data of such identified light points.

BACKGROUND OF THE INVENTION

Surgical operations or radiotherapy are being performed increasingly with the aid of so-called navigation or tracking systems. Patient data is determined using an imaging technique, for example, a computer tomography or magnetic nuclear resonance tomography, which can be used to indicate to the treating surgeon by means of a display output where his treatment tool is momentarily located. For example the position of the tip of an instrument within a part of the body to be treated can be displayed in order to be able to precisely operate at the places to be treated.

To enable such a navigation system to function, the momentary location of the patient or the part of the body to be treated needs to be known in situ during treatment. This updated positional data can then be assigned to the data received from the imaging process, for example, the data from a computer tomograph produced some time prior to treatment. After this assignment, the computer-assisted treatment may commence.

RELATED ART

US 2002/0002330 A1 discloses a method for referencing a patient or a patient body part in a camera-assisted, medical navigation system comprising the following steps: the patient body part to be referenced is brought into the detecting range of a navigation system assisted by at least two cameras, this navigation system detecting with computer support the three-dimensional, spatial positions of light marks; light marks are generated on the surface of the part of the body to be referenced by means of a light beam, the three-dimensional position of the light marks being determined by the camera-assisted navigation system; the three-dimensional position of the surface of the part of the body to be referenced is determined by means of the positional data for the light marks.

US 2012/0229622 A1 discloses an eye-safe, long range laser pointer system using a short pulse laser and a gated camera to detect the laser spot at long ranges in the presence of a strong solar background. The camera gate is synchronized with incident laser pulses using a separate large area, fast photodiode to detect the high-peak power pulses. Alternately, gate synchronization using a GPS-disciplined clock can be used.

U.S. Pat. No. 6,346,933 B1 discloses an interactive presentation control system, used with a display computer, a computer-controlled image projector, a laser pointer, and a projection screen, which comprises a digital camera and a control module. The display computer generates electronic images which are projected onto the projection screen as presentation images. During operation, a presenter uses the laser pointer to trace out a pre-established gesture spatial pattern onto the presentation image. The digital camera acquires these presentation images from which images a processing section in the control module analyzes and identifies the gesture spatial pattern. The identified gesture spatial pattern is compared to a set of pre-established patterns to find a match and to subsequently select a correlated display command. The display command, which can be executed within the control module or transmitted to the display computer, changes the presentation image by an action such as: advancing to the next image, highlighting a text segment, or zooming in on the image.

CN 101419513 A discloses an infrared laser pointer remote pointing and virtual touch system being composed of a computer system, and infrared laser pointer, an image acquisition device and an image identification positioning module. The computer system comprises a display device and a mainframe computer. The infrared laser pointer is provided with an infrared laser emitting key and can emit an infrared laser to point to a display screen. The image acquisition device is arranged in front of the display device to completely contain the display screen in the view finder range. The image identification positioning module identifies an infrared laser point and the position thereof in the display screen according to the acquired image, differentiates different operations including light spot instruction, light spot movement and clicking according to the time length and the times of the infrared laser, and controls the computer system to generate a light spot at the corresponding position on the display screen and completes the corresponding operation. The disclosed system is especially suitable for large-screen display equipment.

DEFINITIONS

Data Processing Method

The method in accordance with the invention is for example a data processing method. The data processing method is for example performed using technical means, for example a computer. The data processing method is for example constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is for example connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is for example operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Acquiring Data

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. For example, the acquiring step does not involve an invasive step which would represent a substantial physical interference with the body, requiring professional medical expertise to be carried out and entailing a substantial health risk even when carried out with the required professional care and expertise. For example, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then For example referred to as "XY information" and the like.

Computer

The method in accordance with the invention is for example at least partly executed by a computer, i.e. all the steps or merely some of the steps (i.e. less than the total number of steps) of the method in accordance with the invention can be executed by a computer.

Registering

The n-dimensional image of a body is registered when the spatial location of each point of an actual object within a space, for example a body part in an operating theatre, is assigned an image data point of an image (CT, MR, etc.) stored in a navigation system.

Image Registration

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Computer Program Product, Signal Wave

The invention also relates to a program which, when running on a computer, causes the computer to perform one or more or all of the method steps described herein and/or to a program storage medium on which the program is stored (for example in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is for example a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker for example has a spherical and/or spheroid shape and can therefore be referred to as a marker sphere; markers can however also exhibit a cornered, for example cubic, shape.

Pointer

A pointer is a device which can emit light, such as a laser beam, on a surface or a part of the body, wherein a user directs or points the pointer (for example, a tip of the pointer which emits light) to a surface, such that the emitted light generates a point, mark or spot on the surface, which causes a reflection such that the 3D position of the point or spot can be determined by using a surgical navigation system. The surgical navigation system then can for example determine the shape of a surface based on a number of acquired pointer spots or can register the surface to a predetermined shape or body structure, wherein the assignment can be made automatically or by user intervention. The pointer can be synchronized to the camera, e.g. the acquisition or frame rate, and/or can be controlled based on a pre-defined emission pattern to emit light pulses. The pattern of the light pulses can be used to discern the pointer light spots from other light sources or reflections.

Reference Star

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

Navigation System

The present invention is also directed to a navigation system for computer-assisted surgery. This navigation system for example comprises a computer for processing the data provided in accordance with the data processing method as described in any one of the embodiments described herein. The navigation system for example comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer emitting light onto the detection point causing a reflection which can be detected e.g. by cameras of a navigation system. In this way, the absolute point data can be provided to the computer. The navigation system also for example comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

Referencing

Determining the position is referred to as referencing if it implies informing a navigation system of said position in a reference system of the navigation system.

Commercial Use

The invention can be used in connection with the Z-touch® system provided by the applicant and provides the advantage that z-touch spots can reliably be acquired while excluding misinterpretation of other light sources, such as light bulbs, direct reflections of light bulbs, pulsoximeters, IR remote controls, etc. as being z-touch spots. A distortion of the z-touch acquisition by light reflections not originating from the z-touch pointer can thus be avoided.

SUMMARY OF THE INVENTION

The invention provides a data processing method and a laser pointer system for detecting reflections of light pulses, such as (laser) light pulses emitted by a (laser) pointer. The light pulses can be visible light pulses or invisible light pulses, such as infrared light pulses, wherein invisible or infrared light pulses for example be combined with a visible beam.

In case a patient body part is to be referenced or registered, the patient body part is placed in the detecting range of a navigation system, for example assisted by at least two cameras. Light marks are generated or projected onto the surface of the part of the body to be referenced or registered by means of a light beam which can be emitted from a light pointer or laser, which light marks can be detected by a camera as light mark or light pulse reflections.

According to the data processing method performed by a computer for detecting reflections of light pulses, a camera signal is acquired representing a series of camera images or frames of a camera viewing field. The series includes for example at least three frames and can encompass a larger number of frames. It is detected by evaluating the frame sequence whether the camera signal includes one or more light mark portions within the camera viewing field which possibly represent a light pulse reflection.

The detected light mark portions in some or all of the series of camera images or frames are related to or compared to a pre-defined emission pattern of the light pulses emitted by the pointer. The pre-defined emission pattern can for example be a pattern not allowing a light pulse and consequently not allowing a light mark portion or reflection to be present in specific frames of the camera system. For example, the pre-defined emission pattern can define that a pointer beam emitted by the pointer can at most only be present in every n-th camera image or frame, such as in every second frame, while not being present in the frames in between. For example, the pre-defined emission pattern can define that a pointer signal and consequently a light mark portion or reflection is only emitted and—if detected—is at most present in every odd frame while not being present in every even frame.

The data processing method determines that a light mark portion is a reflected light pulse corresponding to an emission of the pointer, if the light mark portion in the series of camera image matches or is equal to the pre-defined emission pattern of the light pulses. If a light mark portion shows a pattern which does not match the pre-defined emission pattern, it is determined that it is not a reflected light pulse and is consequently not recognized as light originating from the pointer.

The pre-defined emission pattern of light pulses emitted by the pointer can be synchronized with the image acquisition of the navigation or tracking system, which also provides the advantage to reduce the average laser power.

The data processing method thus analyzes the time-pattern of light mark portions, such as infrared spots, and determines whether or not the time-pattern fits to the emission pattern of the pointer to uniquely identify a detected light mark portion in a series of camera images to be a reflected light pulse originating from the pointer.

For example, the series of camera images of the camera viewing field is a series of subsequent camera images or frames taken with a fixed or pre-defined idle time interval, such as for example 50 ms, between two camera images. The series can be a series of stereoscopic camera images and can include three-dimensional data which might be reconstructed from the stereoscopic camera images. In case a pre-defined idle time interval is present between two timely adjacent camera images or frames, the light emission of the pointer is for example controlled to allow an emission of a light pulse being present at most during the camera acquisition period and being for example present in less than all acquisition periods, i.e. not being present in at least one frame and for example not being present in specific frames being defined by a pre-defined emission pattern. The pre-defined emission pattern can be any arbitrary pattern defining that at least one frame of the camera acquisition signal is defined in which no light pulse is emitted by the pointer. The pre-defined emission pattern can be a periodic (binary) pattern of an arbitrary length and/or can be an arbitrary (binary) pattern which may be repeated periodically.

For example, the pre-defined emission pattern of the light pulses corresponds to every n-th camera image, wherein n is equal to or greater than two, so that the laser light pulse is only seen at most in every n-th camera image or frame. If n=2, a light reflection or laser spot can be found in a frame with an odd (or even) frame number, whereas no light reflection or laser spot can be found in a frame with an even (or odd) frame number. n can be any number such as 2, 3, 4, 5, . . . .

For example, a match of the light mark portion in the series of subsequent camera images to the pre-defined emission pattern of the light pulses is detected, when the light mark portion is only detected in all or some of the camera images corresponding to the emissions according to the pre-defined emission pattern of the light pulses and is not detected in the camera images corresponding to the period(s) of no emission in the pre-definition emission pattern of the light pulses. Thus, if a light mark portion is present in one or more camera frames which do not allow a reflection to be present in accordance with the predefined emission pattern, it is decided that the light mark portion is not originating from the light pointer and is thus not to be considered as a reflection.

The light pointer can be synchronized with the camera system, for example by detecting light signals or light pulses emitted by light sources provided at or close to the camera(s) in order to control the light pointer not to emit a light pulse during a period of no detection of the cameras, i.e. between two timely adjacent frames, and—depending on the pre-defined emission pattern—to emit a light pulse or not during a period of acquiring a camera image or frame. The camera system is thus independent of the light pointer, whereas the light pointer is synchronized or gated based on a signal from the camera defining a camera acquisition period and/or a camera idle period. The signal provided to the light pointer can be an optical signal or can be provided in other form, such as an electronic signal, provided by wire or radio communication.

For example, a light mark portion in the series of camera images is only determined to be a reflected light pulse, if the light mark portion can be detected m-times in a number of n consecutive camera images, wherein n≥3 and m<n. Thus, the pre-defined emission pattern uses at least three camera images or frames and at least one of the n frames includes no light mark portion. This predefined emission pattern consisting for example in its basic structure of n=3 frames can be applied periodically, so that for example every third frame allows for a light pulse whereas the other two frames do not allow light pulses to be present. Alternatively, every third frame allows no light pulse, whereas light pulses are allowed in the other two frames in between. Based on such basic pre-defined emission patterns, controlling the emission of light by the light pointer can be periodically to provide triples, quadruples . . . of emitted light pulses having a pre-defined emission pattern and being continuously repeated to provide the pre-defined emission pattern being the basis for detecting reflections of light pulses. This allows to distinguish between light signals originating from light pulses emitted by the light pointer following the pre-defined emission pattern and light signals originating from other sources not following the pre-defined emission pattern.

For example a number is defined specifying how many reflection signals have at least to be detected in a sequence of n consecutive frames in order to be considered as a possible reflection to ensure sufficient visibility, the number can e.g. be 3 or more.

For example, a light mark portion in the series of camera images is only determined to be a reflected light pulse, if two subsequently detected light mark portions are determined not to have more than a pre-defined maximum distance. Since the light pointer is allowed to be moved in order to determine or register a surface, a light pulse reflection in a frame can be shifted or located apart from a reflection being present in a previous camera frame. Setting a pre-defined maximum distance between light mark portions detected in two subsequent frames defines a maximum speed of the light mark on the object or surface in order to be recognized as a reflection. Setting the maximum distance for example at 0.5 cm and using a camera system acquiring camera images or frames every 50 ms while allowing the light beam to be present only in every second frame leads to a maximum speed of 0.5 cm/(2×50 ms)=5 cm/sec.

Depending on the set parameters like frame rate and predefined emission pattern, other maximum speeds can be defined to limit the acquisition of light spot detection.

For example, a light mark portion in a series of camera images is only determined to be a reflected light pulse, if a single reflected light pulse is identified in a camera image. This is advantageous in case only a single light pointer is used. If by incident more than a single, for example two light mark portions are detected, which both match the predefined emission pattern and optionally also match the above-mentioned maximum speed criterion, it can then be determined that no clear identification of the correct reflection is possible, so that no detection is made. The same principle can be applied when using two, three or more light pointers by defining that at most as many reflections can be present as light pointers are used.

According to a further aspect, a method for determining a shape of a surface or registering a surface to a given or predetermined shape using a medical navigation system is provided. The shape determination or registration is provided in three dimensional space and can for example be used for referencing or registering a patient or a patient body part. Light marks are generated on the surface, such as the surface of a part of a body to be referenced or registered, by means of a light beam which can be emitted by a light pointer, such as a laser light pointer. The laser light pointer emits light pulses following a pre-defined emission pattern as described above and is for example synchronized to the camera system to for example not emit light signals between camera frames and during the acquisition of camera frames in which it is not allowed that a light spot is present when following the pre-defined emission pattern. A data processing method as described above is performed by a computer to detect light pulse reflections. Based on the detected light pulse reflections, three-dimensional, spatial positions on the surface are determined using the navigation system. Based on the positional data of the detected light pulse reflections, the shape of the surface can be determined or a surface can be registered to a shape.

According to a further aspect, a laser pointer system is provided comprising a laser pointer element which comprises a detection element which can detect a control signal, such as a light detection element, and further comprises a laser controller coupled to the detection element and a laser coupled to the laser controller. A camera system comprises a transmission element for transmitting a control signal, such as a lighting element for sending an optical signal or a transmitter capable of sending a radiocommunication signal, and a camera. A camera control unit is provided for controlling the camera system. The camera control unit controls the transmission element of the camera system, such as a lighting element, to emit a defined pattern of control pulses which can be light pulses. The light pulses can serve the purpose of illuminating the field of view of the camera and can additionally be used to control or trigger the laser pointer element. The control signal or light pulses can be synchronous with the data acquisition period of the camera(s), e.g. being "ON" during the period of acquiring a frame. It is also possible to transmit the control signals or control information from the camera system to the laser pointer element without using light signals, such as by radiocommunication or using a wire. The laser controller receives a detection signal from the detection element and controls the laser to emit a pattern of pointer beams or pointer light pulses being at least in part or fully dependent on the detection signal, so as to synchronize the pattern of pointer beams or pointer light pulses to the defined pattern of control pulses or light pulses emitted by the transmission element of the camera system. For example, the detection signal received by the laser controller from the camera system is the basic control signal for controlling the emissions of the laser, wherein the pre-defined emission pattern which is known to both, the laser controller and the unit evaluating the camera signals, e.g. the camera control unit, is additionally considered by the laser controller when deciding whether or not a light signal or light pulse is to be emitted by the laser. The laser controller can be understood as to modulate the pre-defined emission pattern onto the control pulses received from the camera system, i.e. the control pulses of the camera system can e.g. define the time sequences of acquiring the frames and the pre-defined emission pattern defines in which of the acquired frames a light pulse is emitted and in which of the acquired frames no light pulse is sent.

For example, the laser pointer system comprises a stereoscopic camera system comprising at least two separate cameras in order to acquire three-dimensional (3D) information in the known manner. In case a light mark can be seen by at least two cameras, the 3D position of this light mark can be determined.

When operating the above described laser pointer system, the laser pointer element can issue a signal, such as for example a visible, audible or tactile signal, in case the laser pointer element detects that it is triggered or synchronized with the camera acquisition pattern (e.g. a green light) and/or issues a signal (e.g. a red light) as mentioned above in case the laser pointer element detects that it is not triggered.

Thus, it can be signalled to a user whether or not the laser pointer element is ready to use or whether it has to be synchronized with the camera system (again).

For example, the laser pointer element modifies a defined pattern of light pulses to transmit an information to the camera system. The information can relate to the battery status, the position or an acceleration of the laser pointer element measured within or at the laser pointer element. The information can for example specify a distance to a surface measured at the laser pointer element.

In order to transmit the above mentioned information, the data to be transmitted can be embedded in a predefined data frame comprising for example a fixed header (e.g. defined pulses in a number of frames), followed by the data, followed by a trailer which can for example contain a check sum to check whether the received data was correctly acquired. While it is understood, that there is no pre-defined emission pattern during the transmission of arbitrary data such as mentioned above, the acquired light mark portions can nevertheless be used for detecting reflections which can be done retrorespectively, for example after the check sum was received and confirmed that the transmitted data is correct. In addition or alternatively, data to be transmitted can be distributed over a number of frames and can be sent or included in frames which have no "meaning" within the pre-defined emission pattern, i.e. the pre-defined emission pattern does not define whether or not a light signal has to be present in the respective specified frames and thus leaves these frames open for data transmission. For example, several light marks are generated in sequence on the surface wherein the pre-defined emission pattern, which also can provide for "blank" frames to allow data transmission, can be designed to allow at most a number of i subsequent frames which do not contain a light pulse, wherein i can for example be 2, 3, 4, 5 . . . .

Not allowing a too long period of subsequent frames without light signal emitted by the pointer element improves the accuracy of shape determination or registration.

The present invention is defined by the appendant independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

BRIEF DESCRIPTION OF THE DRAWINGS

The components and the Figures are not necessarily to scale, emphasis instead being placed upon illustrating the principles of the invention. The Figures show.

DETAILED DESCRIPTION OF THE PREFERRED EMBODIMENTS

Figure 1:
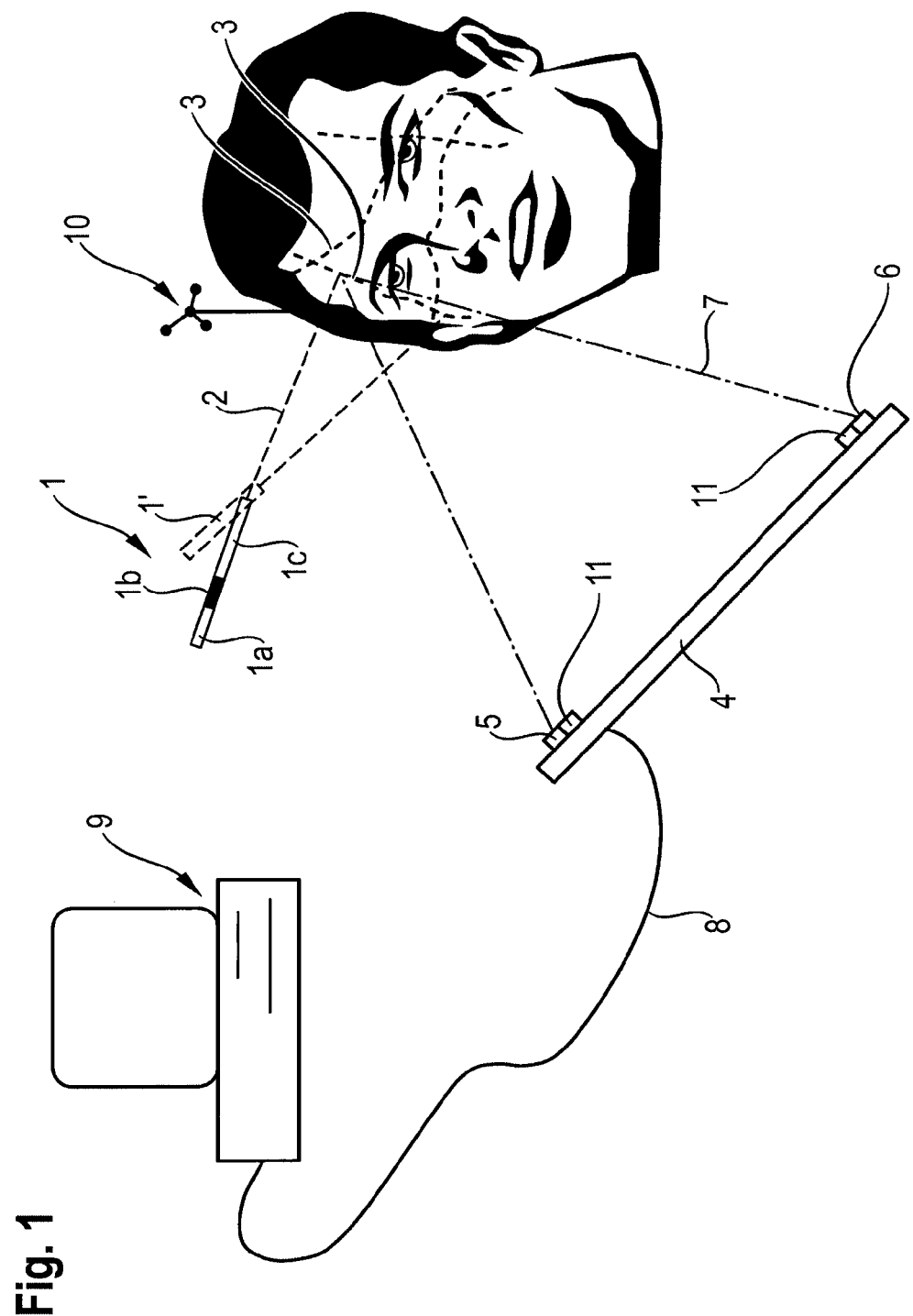
FIG. 1 an embodiment of a laser pointer system.

FIG. 1 illustrates schematically the computer and display of the camera-assisted navigation system, identified as a whole by the reference numeral 9. This computer can also perform the function of the camera control unit and is connected to the camera mount 4 via the cable connection 8. Two infrared cameras 5 and 6 for monitoring the target area being attached to the camera mount 4 spaced apart from each other. Transmission elements 11, such as lighting elements issuing a light or infrared illuminating and control signal to the detection element 1a of the laser pointer element 1 are provided adjacent the cameras 5 and 6.

In this embodiment, it is the position of the human head shown that is to be referenced or registered. For this purpose, use is made of the light beamer 1 being a laser pointer, which projects an infrared laser light beam 2 on the facial surface of the patient. The light beamer 1 is indicated as 1' by the broken line in a second position to indicate its movement during referencing. The light beamer 1 or laser pointer element comprises the mentioned detection element 1a receiving signals from at least one transmission element 11 of the camera system, a laser controller 1b which controls, depending on the control signal received by the detection element 1a and a predefined emission pattern stored within laser pointer element 1 and being known to the camera control unit 9, operation of laser 1c to emit a sequence of laser light pulses 2 onto the object corresponding to the acquisition frames of the cameras 5, 6 and complying with the pre-defined emission pattern.

The facial surface is then scanned by the referencing light beam 2, resulting in light reflections or light spots 3 being produced in sequence on the surface. In the drawing, only a few such light marks are represented by way of example, i.e. by a line of such light spots. However, these spots or reflections may also in general be produced individually at suitable locations by appropriately moving pointer 1, 1'.

Before a later treatment, the person conducting the treatment can simply takes hold of the light beamer 1 and scans the facial surface with the light beam 2 for some time. Due to the fast recording in sequence of single images, the camera system acquires and detects respective light reflections 3 each arranged in sequence, the light path of which for a single light spot is indicated in the drawing by the dot-dash line 7. The two cameras 5, 6 are able to three-dimensionally map the spatial location of the light reflection and the computer system 9 can determine from the data of the detected light marks the position of light spots assigned to the facial surface.

Stored in the computer are the data from a scan of the patient's head, and thus also the data for the facial surface. The computer then continually determines with the aid of a matching routine whether the number of the imaging spots obtained from referencing by means of the light beam is sufficient for it to assign or make congruent the detected surface points of the surface, as known to it from the scan data set. Once sufficient agreement exists, an acoustic and/or visual signal is output to indicate to the person conducting treatment that referencing has been successfully concluded.

The imaging spots 3 generated thus eliminate the need for attached markers or markers otherwise applied, as used hitherto separately. The plurality of light spots 3 obtained makes it possible to perform high accuracy referencing.

Also schematically shown in the figure is that a reference adapter 10 is fixedly positioned to the head of the patient. This adapter comprises three reflectors or markers, the positions of which can be likewise tracked by the cameras 5, 6. Should it now be necessary to turn the head of the patient during referencing or to move the cameras 5, 6, to eliminate camera shades, for instance by the nostril, the relative movement is tracked with the aid of the adapter 10 and taken into account in referencing so that detecting errors are avoided.

The light beamer 1 may project in addition to the invisible (e.g. infrared) light beam 2 also a visible light beam in the same direction and with the same focus to enable the person conducting treatment to keep visual track of the light spots generated and to prevent beaming into the eyes.

The referencing system in accordance with the invention may be employed with all methods of treatment involving an image-assisted operation. This applies to both surgical operations and radiation treatments. Referencing can also be employed for tracking systems with passive marker arrays as well as for those with active emitter markers, as used for instance in tracking medical instruments. Although hitherto it has mainly been indicated that the light marks are generated by means of the light beam on the skin surface of the patient, it is also conceivable within the scope of the invention to reference bone structures already exposed in this way for treatment, for instance, exposed bone portions of the skull or spine.

Figure 2:
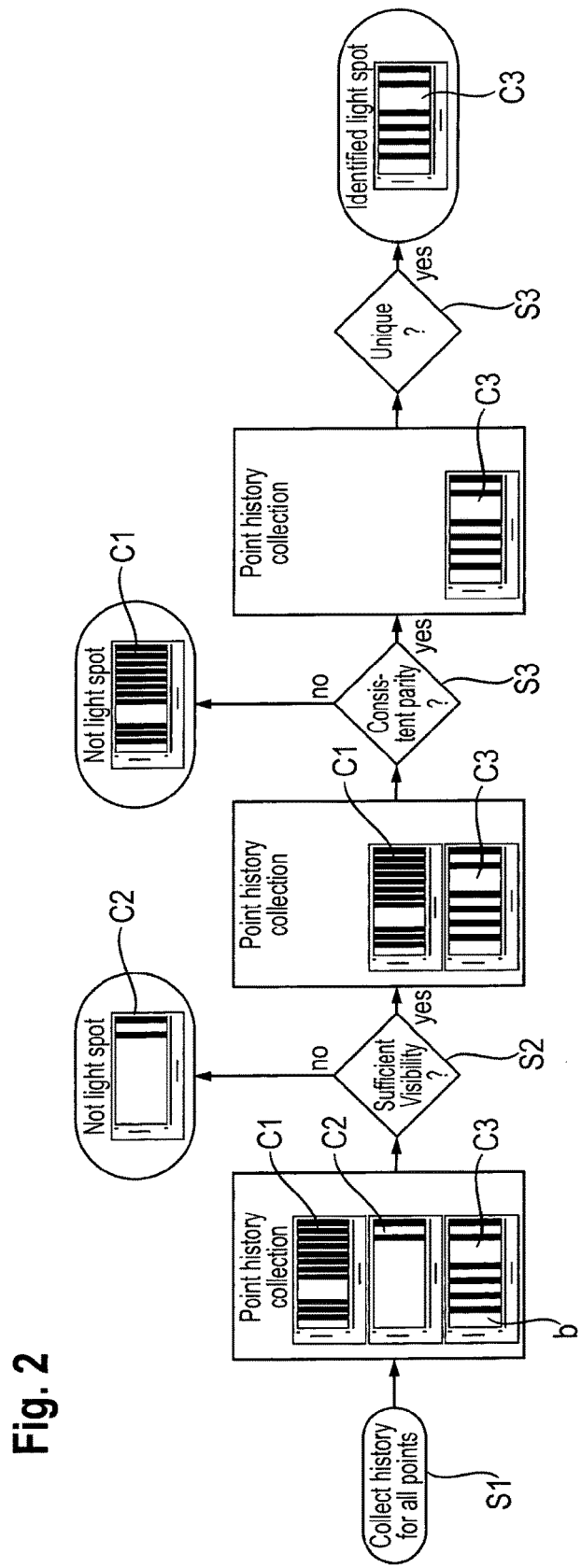
FIG. 2 a flow chart of a data processing method for detecting reflections.

FIG. 2 shows an embodiment of a flowchart for detecting reflections of light pulses.

In a first step S1, all light mark portions within the viewing field of cameras 5 and 6 are collected including the point history for every light mark portion. In the shown example, three light mark portions (candidates C1, C2 and C3) were identified as being possible reflections of pulses emitted by laser 1c. The history collected in step S1 considers according to the embodiment only light mark portions relating to light marks moving on the surface with a speed being below a predefined maximum speed (see FIG. 3).

The bars b shown at the timely adjacent "odd" and "even" frame locations represent a detected light mark or light spot for each possible candidate to be evaluated for being a light pulse reflection of laser 1c or not. The top candidate C1 shown in the point history collection includes three subsequent light spot detections in three subsequent camera frames followed by three missing frames followed by eight subsequent detections. The second candidate C2 includes only two light spot detections separated by a single frame. The third candidate C3 includes light spot detections only in odd frames and has no light spot detection in any even frame.

Step S2 defines whether or not there is a sufficient visibility of light spots. Since the second candidate C2 including only two light spot detections is no reliable basis, this candidate is sorted out as being not a light spot.

Sufficient visibility in step S2 can for example be defined by considering a predefined number of frames, such as in the described example 15 frames, showing at least another pre-defined number of detection signals, such as for example at least four signals within the predefined number of e.g. 15 frames.

Thus, only candidates C1 and C3 remain.

In step S3, it is determined whether or not the remaining candidates C1 and C3 match to the predefined emission pattern being in the present case that the rule that the light beam is issued only in odd frames by laser 1c, whereas laser 1c does not emit a signal in even frames.

Comparing the remaining candidates C1 and C3 with the predefined emission pattern, candidate C1 is sorted out as not being a light spot, since light signals are also present in even frames which might be an indication that these light signals were acquired based on other light sources than the pointer 1.

It follows that there is only a single remaining candidate C3 matching the pre-defined emission pattern. In an optional step S4, it is decided whether the number of remaining candidates matches the number of employed laser pointer elements. Since in the described embodiment a single laser pointer element 1 is used and only a single candidate C3 remains in the point history collection after step S3, candidate C3 is identified as being or corresponding to the reflected light pulse.

Although candidate C3 does not indicate a light reflection in every odd frame, it is nevertheless determined to be or corresponding to the reflected light spots and the missing of a signal is not detrimental to the detection, since a missing signal can result from any kind of distortion, such as for example blocking the line of sight between the laser 1 and the object or between the object and the cameras 5, 6. The criterion leading to the exclusion of a candidate is the presence of light signals in frames which are not allowed to contain light signals according to the pre-defined emission pattern, not the missing of a signal in a "allowed" frame.

Figure 3:
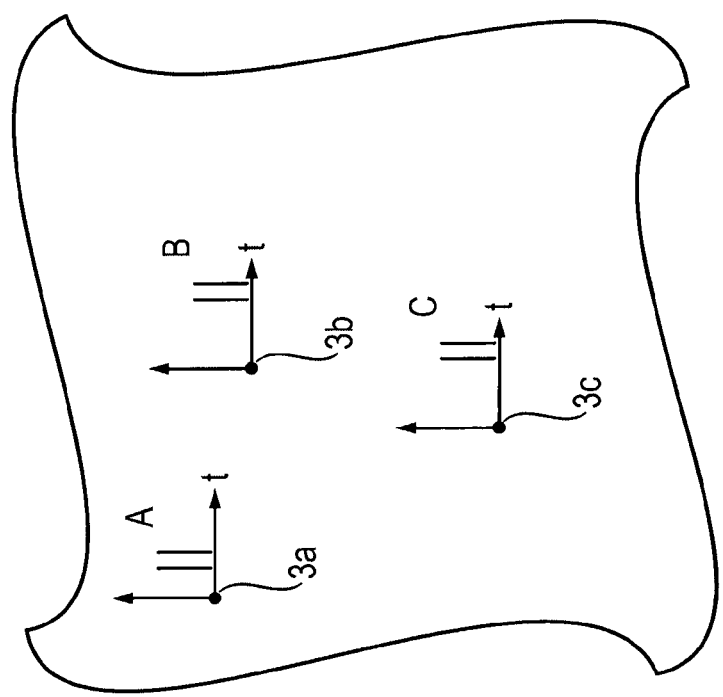
FIG. 3 an embodiment illustrating the principle of detecting reflections considering pre-defined motion constraints.

FIG. 3 shows a surface on which light spots 3a, 3b and 3c were seen by cameras 5, 6 with earlier light spot signals A for light spot 3a, and later light spot signals B and C for light spots 3b and 3c, respectively. All light spot signals 3A, 3B and 3C are considered to meet the pre-defined emission pattern. In the shown example, light spots 3b and 3c show the same later signals B and C and light spot 3b has a smaller distance to light spot 3a than 3c to 3a. If the criterion of the maximum allowable velocity of the light spot 3 on the surface is set appropriately low, it can be decided in the illustrated embodiment that light spot 3b is the light spot originating from laser 1c, since the larger distance of light spot 3c from light spot 3a implies a too large velocity of light spot 3c on the surface leading to the ruling out of this light spot 3c.

The invention claimed is:

1. A method, comprising:
   acquiring, from a camera system, a series of camera images of a camera viewing field;
   detecting whether the series of camera images include a light mark within the camera viewing field, wherein the light mark detected represents a possible light pulse reflection;
   comparing a time pattern of the light mark detected in the series of camera images to a pre-define emission pattern of light pulses; and
   determining that the light mark detected is a reflected light pulse when the time pattern of the light mark detected in the series of camera images matches the pre-defined emission pattern.

2. The method of claim 1, wherein the series of camera images of the camera viewing field is a series of subsequent camera images taken with a pre-defined time interval between two camera images, a series of stereoscopic camera images, or includes 3D data.

3. The method of claim 1, wherein the pre-defined emission pattern of light pulses includes a light pulse during every n-th camera image, wherein n is greater than or equal to 2.

4. The method of claim 1, further comprising determining a match of the time pattern of the light mark detected in the series of camera images to the pre-defined emission pattern of light pulses when the light mark is only detected in camera images that align with emissions in the pre-defined emission pattern of light pulses and the light mark is not detected in camera images corresponding to periods of no emission in the pre-defined emission pattern of light pulses.

5. The method of claim 1, further comprising determining the light mark detected in the series of camera images to be a reflected light pulse when the time pattern of the light mark detected indicates m detections in n consecutive camera images, wherein n is greater than or equal to 3 and m is less than n.

6. The method of claim 1, further comprising determining the light mark detected in the series of camera images to be a reflected light pulse when the time pattern of the light mark includes two subsequent detection within a pre-defined maximum distance.

7. The method of claim 1, determining the light mark detected in the series of camera images to be a reflected light pulse when a single reflected light pulse is identified in a camera image.

8. The method of claim 1, further comprising generating a light mark on a surface via a light beam.

9. The method of claim 8, further comprising determining three-dimensional spatial positions of the reflected light pulse corresponding to the light mark generated on the surface.

10. The method of claim 9, further comprising registering a shape of the surface based on positional data of the reflected light pulse.

* * * * *